United States Patent
Cammilli et al.

(10) Patent No.: US 6,397,109 B1
(45) Date of Patent: May 28, 2002

(54) SINGLE PASS MULTIPLE CHAMBER IMPLANTABLE ELECTRO-CATHETER FOR MULTI-SITE ELECTRICAL THERAPY OF UP TO FOUR CARDIAC CHAMBERS, INDICATED IN THE TREATMENT OF SUCH PATHOLOGIES AS ATRIAL FIBRILLATION AND CONGESTIVE/DILATE CARDIO MYOPATHY

(76) Inventors: Leonardo Cammilli, Via G. Caselli 11, 50100 Florence (IT); Gino Grassi, Via F. Pasqui 31, 50019 Sesto Fiorentino, Florence (IT)

( * ) Notice: Subject to any disclaimer, the term of this patent is extended or adjusted under 35 U.S.C. 154(b) by 0 days.

(21) Appl. No.: 09/470,495

(22) Filed: Dec. 29, 1999

(30) Foreign Application Priority Data

Dec. 23, 1998 (IT) .......................................... FI98A0277

(51) Int. Cl.⁷ .................................................. A61N 1/05
(52) U.S. Cl. ...................................................... 607/123
(58) Field of Search ................................. 607/121, 122, 607/123, 126; 600/381, 375

(56) References Cited

U.S. PATENT DOCUMENTS 5,224,491 A * 7/1993 Mehra
5,954,761 A * 9/1999 Machek et al.
6,161,029 A * 12/2000 Spreigl et al.

* cited by examiner

*Primary Examiner*—Scott M. Getzow
(74) *Attorney, Agent, or Firm*—McGlew and Tuttle, P.C.

(57) ABSTRACT

A single introduction electro-catheter to be used for permanent, semipermanent or termporary cardiac stimulation through the Coronary Sinus. Said electro-catheter featuring the possibility to stimulate from one to four cardiac chambers, according to the preferred stimulation protocol, either in sequence or simultaneously, said catheter being characterized by part or all of the following features.

A) A configuration such to be able to support one, two three or four electrodes, placed on separated segments whenever necessary, said electrodes being placed in contact with the targeted cardiac chambers.

B) A stent structure is permanently tied to the electro-catheter, in its distal portion close to the electrode bearing portion of said lead.

C) The stent structure, and the mated electro-catheter segments will be kept in their compressed form while introduced in the access vein. Such compressed form being of an acceptable diameter for trasvenous introduction.

D) Once the system is advanced to the targeted position in the Coronary Sinus, the stent structure will be expanded, dilating the bifurcation of the lead and pushing the electrodes against the cardiac walls.

E) A suitable pre-curvature (40° . . . 90°) is intrinsically given to the lead body along its length, so to allow for an easy positioning of the whole structure in the Coronary Sinus, as described in FIG. 2.

24 Claims, 5 Drawing Sheets

AD = Right Atria
AS = Left Atria
VD = Right Ventricle
VS = Left Ventricle

AD = Right Atria
AS = Left Atria
VD = Right Ventricle
VS = Left Ventricle

AD = Right Atria
AS = Left Atria
VD = Right Ventricle
VS = Left Ventricle

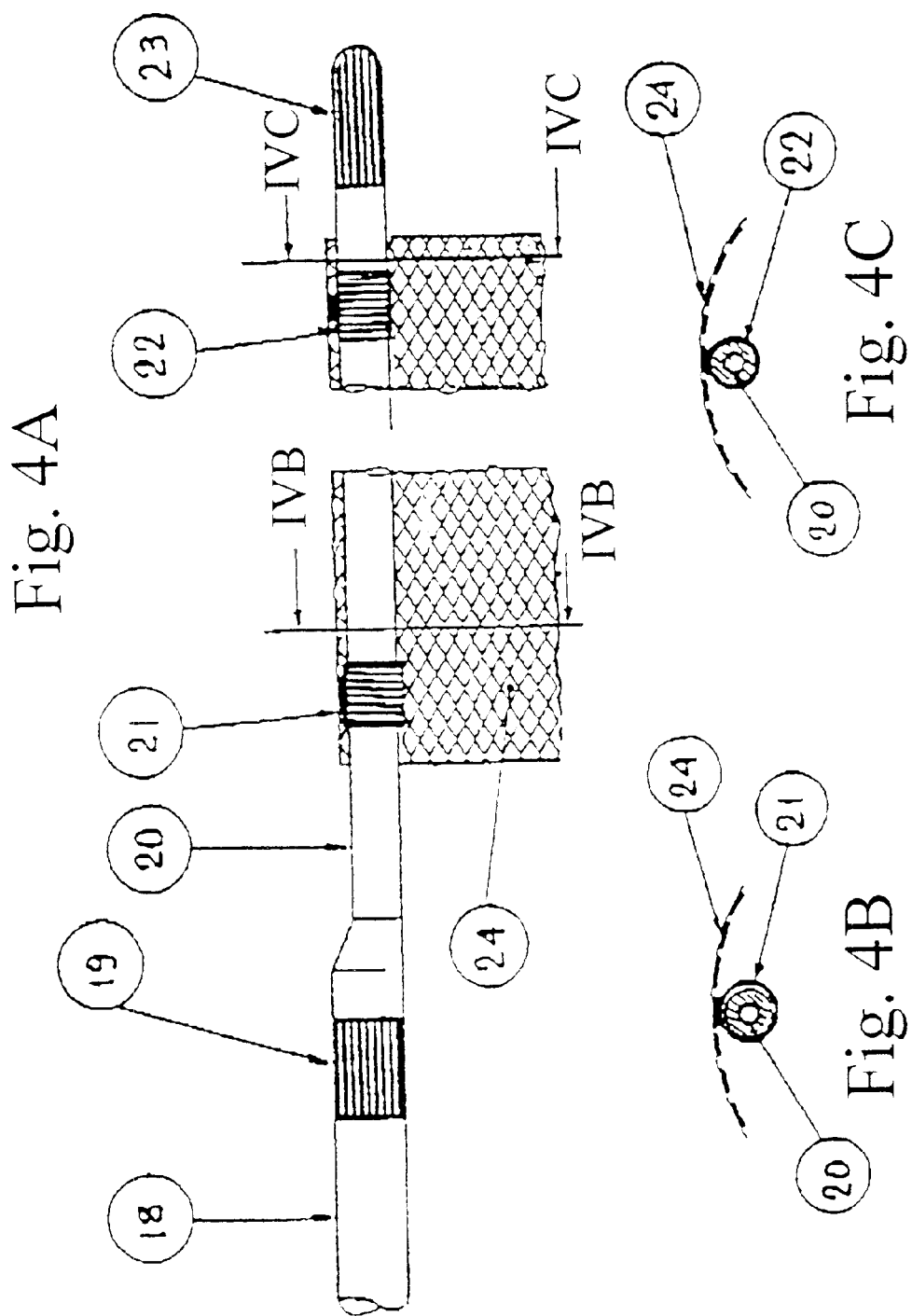

SINGLE PASS MULTIPLE CHAMBER IMPLANTABLE ELECTRO-CATHETER FOR MULTI-SITE ELECTRICAL THERAPY OF UP TO FOUR CARDIAC CHAMBERS, INDICATED IN THE TREATMENT OF SUCH PATHOLOGIES AS ATRIAL FIBRILLATION AND CONGESTIVE/DILATE CARDIO MYOPATHY

BACKGROUND

In clinical electro-physiology there is a growing interest for multisite cardiac pacing intended to be used for prevention and/or therapy of such pathologies as Atrial Fibrillation (AF) and dilative cardio myopathy (DCM).

It has been proven that appropriately timed (sequential and/or simultaneous) somministration of electrical therapy to the different cardiac chambers, up to all four of them, Right Atrium (RA) and Right Ventriculum (RV) and respectively Left Atrium (LA) and Left Ventriculum (LV) can be beneficial to the patients. The appropriate timing of the stimuli shall be chosen according to the appropriate therapy, but it is crucial, to perform such task, that an adequate number of suitable electrical connections be made to every and each heart chamber to be paced and/or defibrillated.

In particular, the above said pathologies are, nowadays, considered as the most likely to experience beneficial effects from multi-site pacing, for said reason the following description will be focused on the above said category of cardiac patients, said particularization not being detrimental to the purpose of disclosure of the general principles underlying the present invention.

Atrial fibrillation (AF) is a fairly common disease, manifesting as a chaotic acceleration of atrial rhythm, comporting loss of atrial and contraction efficacy.

A number of methods have been used to revert such rhythm to sinusal rate (cardioversion), the most used being infusion of anti-arrhythmic drugs and/or electrical cardioversion in a sedate and de-coagulated state.

Such methods, however, cannot control recurrence of AF episodes, while implant of an atrial defibrillator has, as a consequence, highly painful, non tolerable, electrical shock administered to the conscious patient. Implant of a pacemaker featuring multi-site stimulation has therefore been experimented.

DCM, on the other side is a severe illness comporting ventricular life-threatening arrhythmias and contractile cardiac deficiency. The outcome of such pathology being cardiac transplant. Multi-site electrical pacing is used in this pathology as well, aiming to re-synchronization of ventricular contraction.

In order to achieve a multi-site cardiac stimulation it is nowadays mandatory to place an appropriate number (three or more) electro-catheters in the targeted cardiac cavities. Such practice being detrimental to the patient's and operator's safety because of prolonged exposure to x-rays and other possible risks, this not considering the high rate of lead dislodgement and lack of reliability of such a complex wiring system.

The purpose of the present invention is to propose a solution to the problem of multi-site pacing to be less aggressive and more reliable, so to represent a possible alternative even in the general single chamber pacing therapy.

Targeting the said purpose we previously submitted an Italian patent request, number FI/98/A/223, in which we describe an electro-catheter featuring a double spiral pre-formation, to be located in proximity of the atrial chambers and respectively the ventricular chambers, through the coronary sinus.

DESCRIPTION OF THE INVENTION

This invention relates to a method of introducing one or two separate electro-catheter leads in the coronary sinus (CS), such leads being supported by a purpose made structure, similar in shape and function to a coronary "stenting" device. Once introduced and properly placed in the vessel the "stent" structure, bearing the pacing leads, will be expanded in the vessel, thus forcing the stimulating electrodes against the walls of the same.

The most important feature of said electro-catheter system is that it is conceived to be placed in the coronary sinus (CS), thanks to the anatomical characteristics of this vessel. The CS, in fact, is a venous vessel almost cylindrical in shape, whose average diameter in the human is estimated at 15 millimeters and whose length is approximately 30–40 millimeters.

The CS drains most of the venous blood returning from the heart muscle: it is a large vein opening in the right atrium and collects the blood from several smaller veins from different areas of the cardiac walls.

The position in the heart of the CS is basic to the described invention. The coronary sinus path, in fact, starting from its ostium in the right atrium, follows a route along the posterior atrio-ventricular groove, then it follows the groove in its lateral portion, ending its course in the inter-ventricular anterior groove, in the area that separates the two ventricles.

For this reason the CS is characterized by the fact to be in contact, along its antero-superior portion with the posterior wall of the right Atrium, and, after approximately 15–20 mm from the OSTIUM it is in contact with the posterior wall of the Left atrium.

The infero-anterior portion of the CS, in its first portion, is in contact with the posterior wall of the Right Ventricle, while the second portion is in contact with the posterior wall of the left Ventricle, as can be observed in the diagram in FIG. 1.

Said configuration makes it possible to stimulate each and every of the four cardiac chamber through a catheter placed in the CS.

Stability of the lead, pacing reliability, and low stimulation threshold, however, cannot be achieved by use of a standard linear electro-catheter of the type in common use with implantable cardiac pacemakers. The contact of such lead to the aimed walls, in fact, would not be stable, due to the large dimensions of the CS in comparison with the catheter diameter.

The present invention, therefore, is targeted to solve this problem.

The various features of novelty which characterize the invention are pointed out with particularity in the claims annexed to and forming a part of this disclosure. For a better understanding of the invention, its operating advantageous and specific objects attained by its uses, reference is made to the accompanying drawings and descriptive matter in which preferred embodiments of the invention are illustrated.

BRIEF DESCRIPTION OF THE DRAWINGS

In the drawings:

FIG. 4A is a schematic view of an embodiment fixing the electrodes to the stent;

FIG. 4B is a sectional view along line IVB—IVB in FIG. 4A;

FIG. 4C is a sectional view along line IVC—IVC in FIG. 4A;

DESCRIPTION OF THE PREFERRED EMBODIMENT

Figure 1:
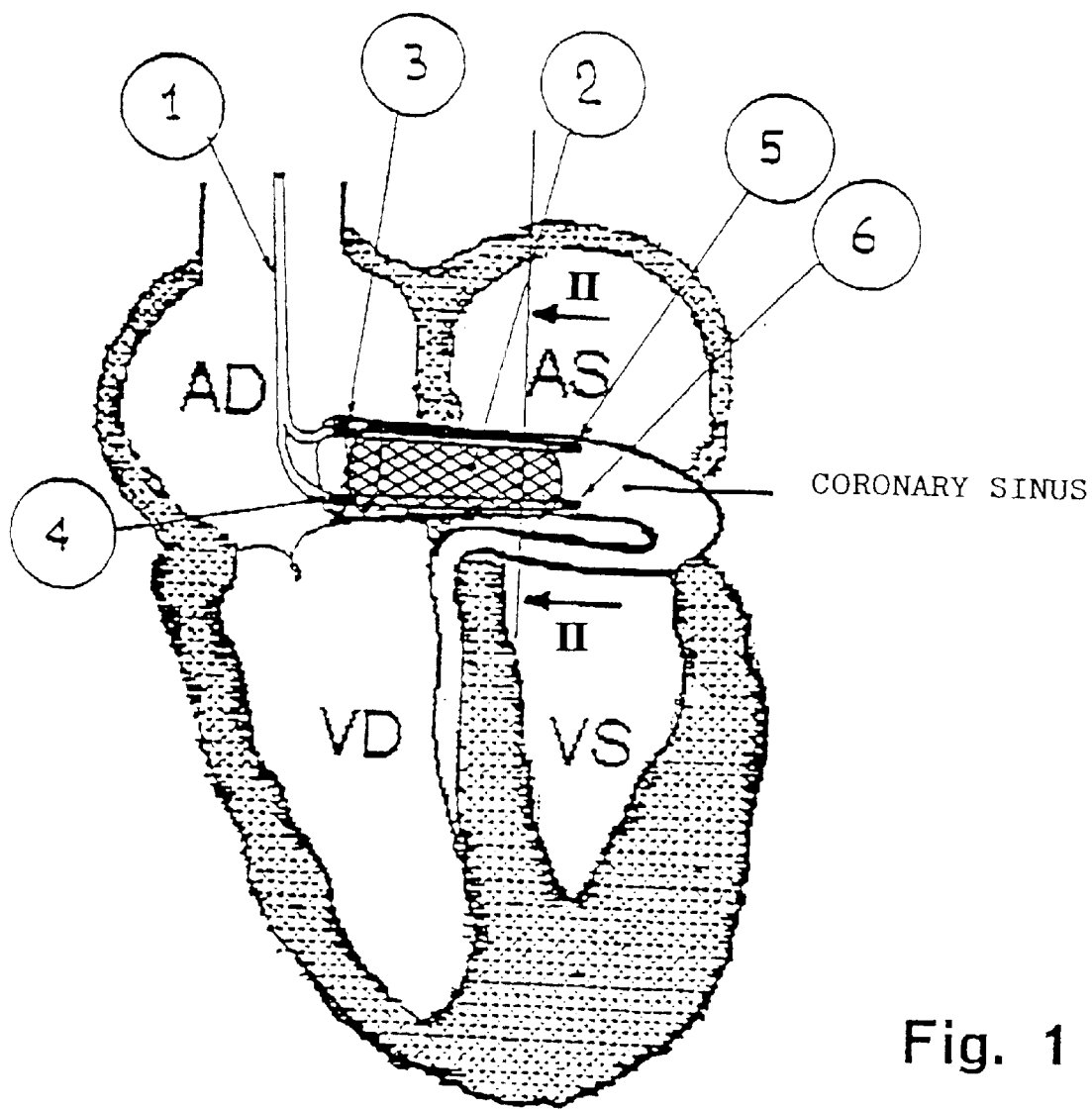
FIG. 1 is a schematic example of a positioning of a stent that supports electrodes for stimulating the four cardiac chambers according to the present invention (in the drawing, AD represents the right atrium, AS the left atrium, VD the right ventricle and VS the left ventricle)

Referring to the drawings, the invention is schematically described in FIG. 1.

The preferred embodiment of the invention, is fabricated as an electro-catheter -1- which, in the portion approaching its entry in the CS, is divided in two parallel branches, bearing the myocardium contacting electrodes.

The branches of the catheter are tied by some suitable means to the internal or external structure of a stent -2- in such a manner that, once the said stent is in its final state, the electrodes carried upon the lead(s) can be in contact of the tissues to be stimulated, in the aforementioned positions and so to be contiguous to the four cardiac chambers: in particular electrodes -3- and -5- shall be respectively in contact with the two atria (Rx and Lx) while electrodes -5- and -6- will be in contact of the two ventricula (Rx and Lx). It is therefore evident that a different number of branches or of electrodes will not affect the underlying basis principle of a stent supported electro-catheter, so that from one to four chambers can be stimulated.

Figure 2:
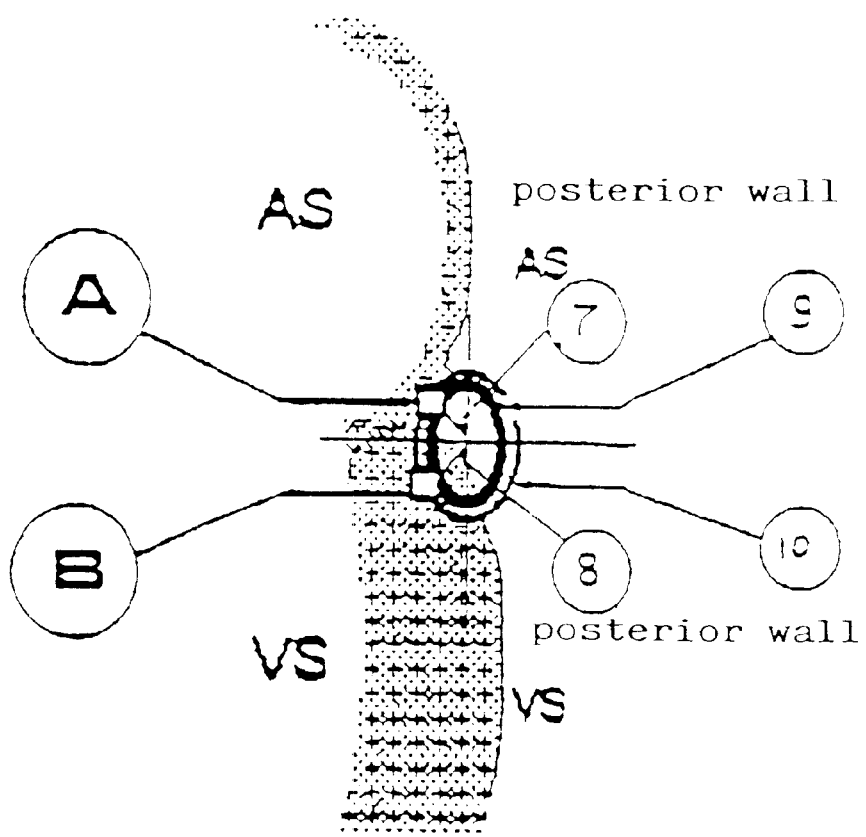
FIG. 2 is a schematic sectional view taken on line II—II of FIG. 1.

When analyzing section X—X of the human heart (FIG. 1) including the CS -10- as is shown in FIG. 2, one can see that the optimal positioning of the electrodes, A towards the atrium and B towards the ventriculum, such to allow for good electrical contact with the tissues to be stimulated, shall be at approximately 45 degree from the vertical axis of the stent section. This is illustrated in FIG. 2, where -9- is the stent section and -7- and -8- represent the Atrial and Ventricular electrodes positioned in contact of the left chambers of the heart. A similar position will be necessary for the corresponding electrodes positioned on the right portion of the heart, now shown in FIG. 2. Said electrodes are spaced from the above shown, longitudinally, in such a manner to be in contact with the right cardiac cavities.

A "stent2 is a medical device, used in trans-luminal angioplasty. It is intended to obviate to stenosys or occlusion of the body arteries, and it consists of a cylindrical or pseudo-cylindrical flexible body, commonly made in the shape of a tube featuring reticular walls, or in any case, made of a flexible, plastic or metallic tubular skeleton.

The device diameter, at the moment of introduction in the vessel, is compressed or reduced in a variable proportion, from ¼ to 1/10 of the diameter of the vessel in which it is intended to be inserted.

Once positioned in its final intended position the stent will be expanded to its final diameter by use of different means, depending from its own fabrication method: as an example it may be left expand simply pushing it from a bearing tube in which it was kept compressed during introduction; or, taking advantage of its possible construction in special 2shape memory" materials (e.g. Nitinol) the stent will be forced to expand by application of thermal energy above a predetermined temperature threshold.

The second approach is possibly the best adapted to the purpose of the invention described here, in that this approach will allow for repositioning and possibly explanting the system in case of malfunction or other clinical necessity.

Figure 3A:
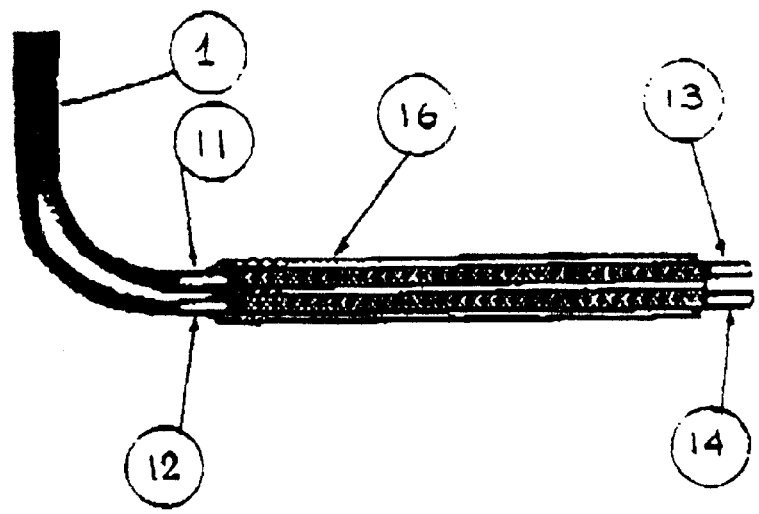
FIG. 3A is a schematic view of the stent of FIG. 1 in its contracted form.
Figure 3B:
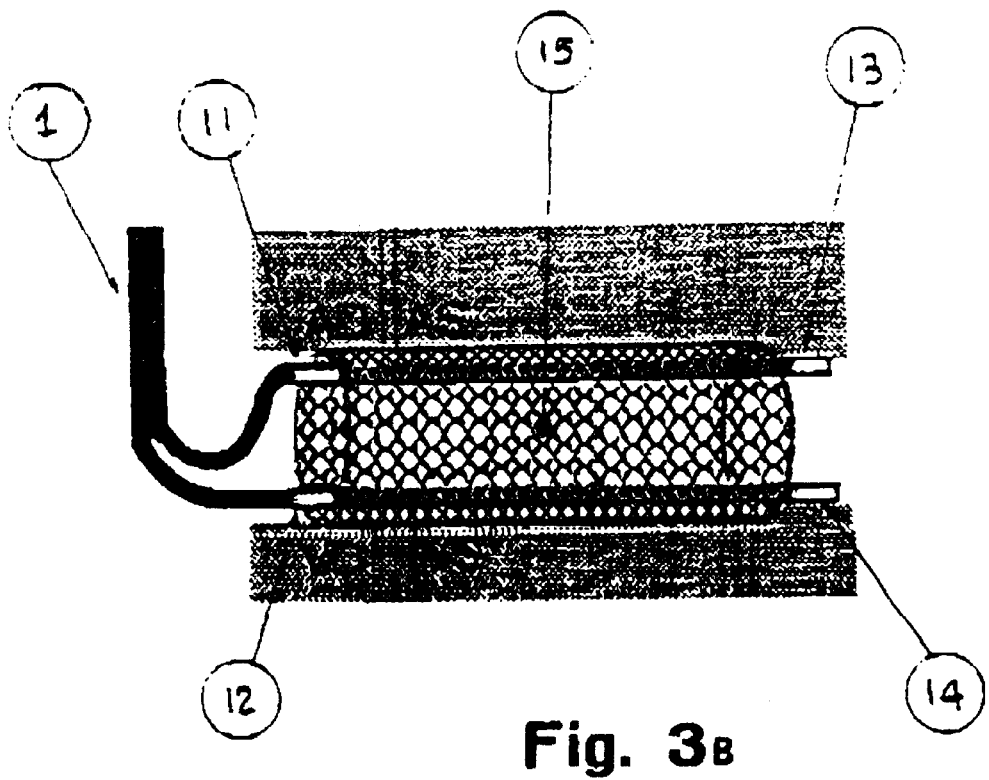
FIG. 3B is a view of the stent of FIG. 3A in an expanded form, and inserted in the coronary sinus.

From the diagram in FIG. 3, one can see that an introduction the proposed electro-catheter will be constrained in a single compact body together with the stent, thus appearing as a single cylindrical or elliptical body, made from the two bifurcated lead segments, said segments being internally or externally tied to the wall of the stent -16- in its contracted form, and said segments bearing the stimulating electrodes -11- -12- -13- -14-.

Once the electrodes will be advanced to the correct position, as described in FIG. 2, such position being radioscopically or ultrasonically verified during the surgical maneuver, the expansion mechanism provided for the stent will be put in action, thus expanding said stent and pushing the electrodes in contact to the tissue(s) to be stimulated.

The major diameter of the whole system, using current technology, may possibly be in the 4 to 7 mm range, which may be considered acceptable for the intended use, although susceptible of improvement towards a small dimension.

One possible solution, which we want to prospect, is the use of insulated electrode conductors interleaved in the stent mesh itself. Such approach should guarantee the minimum possible dimensions of the system, possibly at the expense of a higher fabrication complexity.

In FIG. 3 the catheter -1- is presented as a single body, as shown in FIG. 3a. The catheter shall bear a preformed section, just prior of the section where the electrode bearing bifurcation is placed. Such pre-formed section will ease the correct introduction in the coronary sinus.

Said pre-formation shall be made in a way that the equivalent angle of curvature results in a range from 40° to 90°. Said-pre-formation shall lie in a plane parallel to the one in which the two electrode bearing lead branches are fixed to the stent mesh. Said reciprocal position of the parallel planes is intended to be beneficial to the ease of positioning the whole system in the CS, in the appropriate position as described in FIG. 2.

Each of the bifurcating catheter segments may, in turn, be of bipolar or monopolar nature, that is bear one or two separated poles, the choice being functional to the intended stimulation pattern, eg. Sequential or simultaneous stimulation of the right and the left heart. In any case the portion of each catheter branch entering the stent, and thereby fixed to said stent, will be unipolar, carrying just the conductor necessary for the distal electrode, as shown in FIG. 4.

For the above said reason the diameter of such distal portion of each catheter branch will be reduced in size.

Current technology will easily allow a diameter in the range of 1.2 of 1.5 mm. This does allow for the use of a rather standard multifilar conductor coil which internal diameter of at least 0.45 mm, will permit the introduction of a standard steering stylet. Said steering stylet being necessary to facilitate the final placement of the system.

A representative view of such portion of the system is shown in FIG. 4.

One catheter branch -18- is displayed, said branch being bipolar, thus of larger diameter, up to the point in which it enters the stent mesh, that is up to electrode -19-.

Just past electrode -19- the lead is reduced in diameter, portion -20- carrying a single conductor, up to the distal electrode -23-.

As one can easily see this is the most complete solution, which allows for independent stimulation of the four cardiac chambers, and therefore the resulting diameter of the complete system entering the vein is maximum. A two electrode single conductor system would be much smaller, comporting a single conductor system in each branch, but would only allow for simultaneous stimulation of both the Rx and Lx sections of the heart. Stimulating electrodes -19- and -23- shown in FIG. 4, shall be axially protruding from the compressed stent body, in such a way to be insulated from said body, but in close proximity to the same, so to be obtain a sufficient contact force against the tissue to be stimulated.

When considering the cylindrical mesh stent shape as described in FIG. 3, it appears evident that the expansion of the stent itself will cause a contraction of the longitudinal dimension of the same. The stimulating lead being rigid along this dimension it cannot follow the stent deformation. It is therefore necessary to tie the lead segment to the stent in the special way described in FIG. 4.

A fixed tie -22- is provided preferably but not exclusively to the distal portion of the lead, as shown in FIG. 4 section Y. A sliding frame -21- is fixed to the other lead extremity and to the stent body. This sliding frame may be contained preferably with a system of rings, fixed to the stent mesh, the inner diameter of said rings being larger then the outer diameter of the lead section, thus allowing for reciprocal longitudinal movement of the rings and the lead. The proximal electrode position along the branch segment shall be calculated in a way to keep said proximal electrode fully external to the stent when the system, at introduction, is kept in its compressed state.

Said configuration, as described, shows, at its introduction in the vein, an equivalent diameter that can be considered rather large, in the range of 4 . . . 6 mm. in the zone where the two proximal electrodes are coupled together.

A better solution may be sought by modeling said two electrodes in a favorable shape, e.g. using a section in the shape of a "D", so to minimize the coupled bulk of the two electrodes in this zone. Said shape can be kept by the whole catether in the zone after the bifurcation. Another possibility is to shift slightly the reciprocal position of the mating electrodes so to obtain a better distribution of the bulk resulting from the coupling of said two sections in the compressed state of the stent structure.

In all those cases in which one would only stimulate both atria or both ventricula in a simultaneous modality, or whenever the stimulation of less than four chambers should be required, the overall diameter and bulk of the resulting electrode will be smaller, thanks to the reduced number of conductors and/or to the simplified configuration, while still obtaining the advantages of a stable contact due to the stent fixation means.

As an alternative to the described cylindrical mesh stent one can use a wire structure featuring a "zig-zag" or "criss-cross" mesh and folded so to assume a pseudo-cylindrical shape (FIG. 5), said structure being made of thin elastic (-32-) wire, in oxidable steel or one of suitable "shape memory" materials (e.g. Nitinol).

Said wire diameter would be chosen in the range from 0.15 . . . 0.3 mm.

Figure 5A:
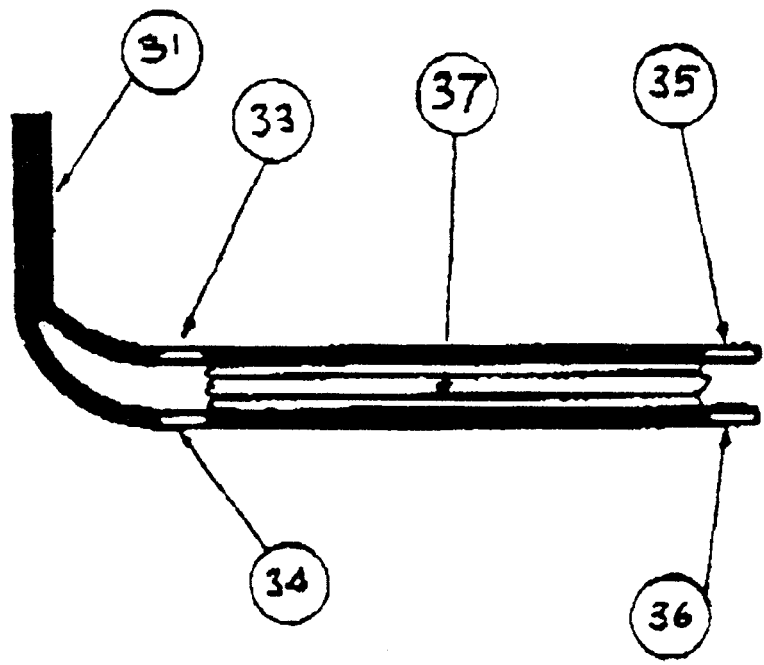
FIG. 5A is a schematic view of another embodiment of the stent of FIG. 1 represented in a contracted form.
Figure 5B:
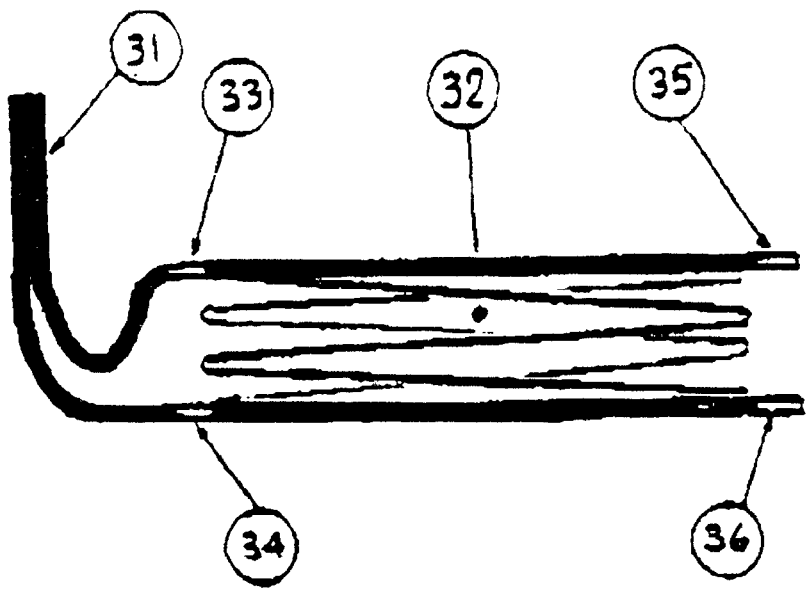
FIG. 5B is a schematic view of another embodiment of the stent of FIG. 1 represented in an expanded form.

The wire structure shall be compressed on itself (-37-) as shown in FIG. 5a at the introduction in the vein, and shall be expanded pressing against the vessel wall once properly placed in situ (FIG. 5b).

Using said configuration the two electrode bearing catheter segments shall be permanently tied to two corresponding segments of the folded elastic wire, so that said electrodes will be positioned as shown in FIG. 2 once the structure is expanded.

The advantage of said configuration being the absence of the above described reciprocal sliding of the structures involved in the expansion. Said advantage will result from the fact that no longitudinal shortening of the structure will occur.

While specific embodiments of the invention have been shown and described in detail to illustrate the application of the principles of the invention, it will be understood that the invention may be embodied otherwise without departing from such principles.

What is claimed is:

1. A single introduction electro-catheter arrangement to be used for permanent, semi-permanent or temporary cardiac stimulation through a coronary sinus in a stimulation protocol that provides to stimulate from one to four cardiac chambers, the electro-catheter comprising:
an electro-catheter with a body presenting a distal portion apt to be inserted through the coronary sinus;
one or more electrodes;
a support structure comprising a stent firmly tied to said electro-catheter at said distal portion, said stent being fixed to said one or more electrodes, a shape of said stent being changeable to assume a first or compressed configuration, in which said stent can be inserted in the coronary sinus, said shape of said stent being changeable into a second or expanded configuration placeable of said one or more electrodes in contact with corresponding one or more cardiac walls of cardiac chambers of the user, said one or more electrodes being supported by electrode bearing segments one of internally or externally tied to said support structure of said stent.

2. A single introduction electro-catheter arrangement according to claim 1, wherein said body of said electro-catheter has a pre-curvature between 40 to 90 degrees along its length, to allow for positioning of said electro-catheter in the coronary sinus.

3. A single introduction electro-catheter arrangement according to claim 1, wherein said one or more electrodes include bio-compatible materials, with high mechanical strength.

4. A single introduction electro-catheter arrangement according to claim 1, wherein said one or more electrodes include bio-compatible materials, with high mechanical strength, a coiled shape, and placed coaxially within an insulating sleeve.

5. A single introduction electro-catheter arrangement according to claim 1, wherein said one or more electrodes include bio-compatible materials, with high mechanical strength, a coiled shape, and placed radially within an insulating sleeve.

6. A single introduction electro-catheter arrangement according to claim 1, wherein said stent has a tubular reticular shape with elastic features.

7. A single introduction electro-catheter arrangement according to claim 1, wherein said stent is made with a folded wire frame with elastic features.

8. A single introduction electro-catheter arrangement according to claim 1, wherein said stent is made of plastic material with elastic features.

9. A single introduction electro-catheter arrangement according to claim 1, wherein said stent is made of metallic material with elastic features.

10. A single introduction electro-catheter arrangement according to claim 1, wherein said stent is made with a tubular reticular shape and has shape memory behavior.

11. A single introduction electro-catheter arrangement according to claim 1, wherein said stent is made with a folded wire frame having shape memory behavior.

12. A single introduction electro-catheter arrangement according to claim 1, wherein said stent is made of plastic material having shape memory behavior.

13. A single introduction electro-catheter arrangement according to claim 1, wherein said stent is made of metallic material having shape memory behavior.

14. A single introduction electro-catheter arrangement to be used for permanent, semi-permanent or temporary cardiac stimulation through a coronary sinus in a stimulation protocol that provides to stimulate from one to four cardiac chambers, the electro-catheter comprising:

an electro-catheter with a body presenting a distal portion apt to be inserted through the coronary sinus;

one or more electrodes;

a support structure comprising a stent firmly tied to said electro-catheter at said distal portion, said stent being fixed to said one or more electrodes, a shape of said stent being changeable to assume a first or compressed configuration, in which said stent can be inserted in the coronary sinus, said shape of said stent being changeable into a second or expanded configuration placeable of said one or more electrodes in contact with corresponding one or more cardiac walls of cardiac chambers of the user, wherein said stent has reticular cylindrical shape and the electrodes are supported by electrode bearing segments tied to an expandable structure in said stent.

15. A single introduction electro-catheter arrangement according to claim 14, wherein said stent has shape memory behavior.

16. A single introduction electro-catheter arrangement according to claim 14, wherein said stent is made of plastic material having shape memory behavior.

17. A single introduction electro-catheter arrangement according to claim 16, wherein said stent is made of metallic material having shape memory behavior.

18. A single introduction electro-catheter arrangement to be used for permanent, semi-permanent or temporary cardiac stimulation through a coronary sinus in a stimulation protocol that provides to stimulate from one to four cardiac chambers, the electro-catheter comprising: an electro-catheter with a body presenting a distal portion apt to be inserted through the coronary sinus;

one or more electrodes;

a support structure comprising a stent firmly tied to said electro-catheter at said distal portion, said stent being fixed to said one or more electrodes, a shape of said stent being changeable to assume a first or compressed configuration, in which said stent can be inserted in the coronary sinus, said shape of said stent being changeable into a second or expanded configuration placeable of said one or more electrodes in contact with corresponding one or more cardiac walls of cardiac chambers of the user, wherein said stent has a folded wire frame structure and the electrodes are supported by electrode bearing segments tied to terminating arms of said wire frame.

19. A single introduction electro-catheter arrangement according to claim 18, wherein said stent has shape memory behavior.

20. A single introduction electro-catheter arrangement to be used for permanent, semi-permanent or temporary cardiac stimulation through a coronary sinus in a stimulation protocol that provides to stimulate from one to four cardiac chambers, the electro-catheter comprising:

an electro-catheter with a body presenting a distal portion apt to be inserted through the coronary sinus;

one or more electrodes;

a support structure comprising a stent firmly tied to said electro-catheter at said distal portion, said stent being fixed to said one or more electrodes, a shape of said stent being changeable to assume a first or compressed configuration, in which said stent can be inserted in the coronary sinus, said shape of said stent being changeable into a second or expanded configuration placeable of said one or more electrodes in contact with corresponding one or more cardiac walls of cardiac chambers of the user, wherein the electrodes are supported by electrode-bearing segments realized by a single conductor with a reduced diameter of 1.1 to 9.6 mm, said reduced diameter allowing a diameter of 3 to 7 mm for said distal portion of the electro-catheter.

21. A single introduction electro-catheter arrangement according to claim 20, wherein said stent is made with a tubular reticular shape and has shape memory behavior.

22. A single introduction electro-catheter arrangement according to claim 20, wherein said stent is made with a folded wire frame having shape memory behavior.

23. A single introduction electro-catheter arrangement according to claim 20, wherein said stent is made of plastic material having shape memory behavior.

24. A single introduction electro-catheter arrangement according to claim 20, wherein said stent is made of metallic material having shape memory behavior.

* * * * *

UNITED STATES PATENT AND TRADEMARK OFFICE
CERTIFICATE OF CORRECTION

PATENT NO. : 6,397,109 B1
DATED : May 28, 2002
INVENTOR(S) : Cammilli et al.

It is certified that error appears in the above-identified patent and that said Letters Patent is hereby corrected as shown below:

<u>Title page,</u>
Please insert Item,
-- [73] Assignee:  Avio Maria Perna (Partial Assignee)
Via Stoppani, 38-Firenze, Italy --

Signed and Sealed this

Fourteenth Day of October, 2003

JAMES E. ROGAN
*Director of the United States Patent and Trademark Office*